United States Patent
Eder et al.

[11] 4,001,302
[45] Jan. 4, 1977

[54] 9,10-SECOESTRANE DERIVATIVES AND THEIR PRODUCTION

[75] Inventors: Ulrich Eder; Gregor Haffer; Jürgen Ruppert; Gerhard Sauer; Rudolf Wiechert, all of Berlin, Germany

[73] Assignee: Schering Aktiengesellschaft, Berlin & Bergkamen, Germany

[22] Filed: Apr. 21, 1975

[21] Appl. No.: 570,091

Related U.S. Application Data

[63] Continuation-in-part of Ser. No. 409,235, Oct. 24, 1973, Pat. No. 3,890,391.

[30] Foreign Application Priority Data

Oct. 25, 1972   Germany ................. 2253089

[52] U.S. Cl. .................. 260/479 R; 260/340.9; 260/346.2 M; 260/476 C; 260/488 CD
[51] Int. Cl.² ......................... C07C 69/02
[58] Field of Search ......... 260/340.9, 340.7, 468 R, 260/476 C, 488 CD, 479 R, 469

[56] References Cited
UNITED STATES PATENTS 3,637,754   1/1972   Bucourt et al. ............. 260/340.7 X
3,647,821   3/1972   Los .......................... 260/340.9

Primary Examiner—Ethel G. Love
Attorney, Agent, or Firm—Millen, Raptes & White

[57] ABSTRACT

9,10-Secoestranes, useful as intermediates in the total synthesis of steroids, of the formula

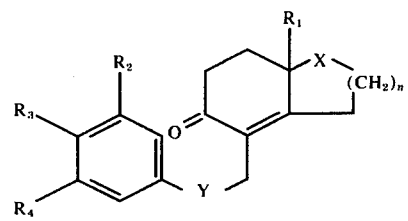

wherein $n$ is 1 or 2, $R_1$ is lower alkyl, $R_2$, $R_3$ and $R_4$ are hydrogen, alkoxy or acyloxy, X is free or ketalized carbonyl or free, esterified or etherified hydroxymethylene, and Y is carbonyl or dialkoxymethylene are produced by condensing, in the presence of a basic catalyst,

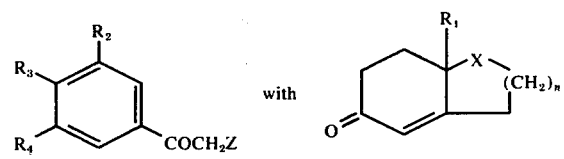

wherein X, $n$, $R_1$, $R_2$, $R_3$, $R_4$ have the values given above, and Z is Cl, Br or I, to produce a 9,10-secoestrane of the above formula wherein Y is a free carbonyl group, which can then, if desired, be ketalized to a corresponding compound wherein Y is dialkoxymethylene or like ketal group.

4 Claims, No Drawings

9,10-SECOESTRANE DERIVATIVES AND THEIR PRODUCTION

BACKGROUND OF THE INVENTION

This invention relates to a process for the preparation of 9,10-secoestrane derivatives. This is a continuation-in-part of application Ser. No. 409,235, filed Oct. 24, 1973, now U.S. Pat. No. 3,890,391.

SUMMARY OF THE INVENTION

According to this invention 9,10-secoestranes of the general Formula I

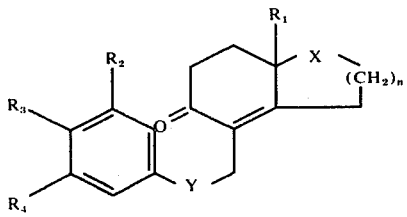

wherein $n$ is the integer 1 or 2; $R_1$ is lower alkyl; $R_2$, $R_3$ and $R_4$ are alike or different and each is a hydrogen atom, alkoxy, or acyloxy; X is free or ketalized carbonyl or a free or ketalized carbonyl or a free, esterified or etherified hydroxymethylene, and Y is carbonyl or dialkoxymethylene; are produced by condensing a compound of general Formula II

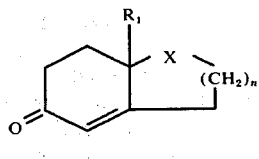

wherein $n$, $R_1$ and X have the values given above, in the presence of a basic catalyst, with an ω-haloacetophenone of general Formula III

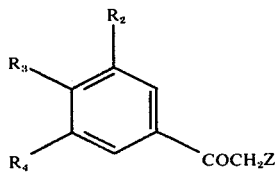

wherein $R_2$, $R_3$ and $R_4$ have the values given above and Z is a chlorine, bromine or iodine atom, to obtain a 6-oxo-9,10-secoestrane derivative of general Formula I, i.e., a compound wherein Y is carbonyl, and thereafter optionally converting these 6-oxo compounds with an alcohol in the presence of an acidic catalyst into the corresponding 6,6-dialkoxy-9,10-secoestrane and like derivatives of general Formula I wherein Y is a ketalized carbonyl group.

In its composition aspect, this invention relates to the 9,10-secoestrane derivatives of general Formula I wherein $n$ is 1, i.e., compounds of Formula Ia

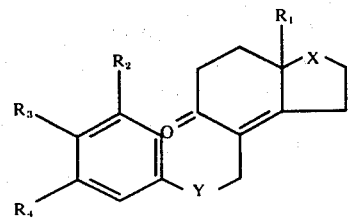

wherein $R_1$, $R_2$, $R_3$, $R_4$, X and Y have the same values as in Formula I.

DETAILED DISCUSSION

Preferred compounds of Formula I are those wherein
a. $n$ is 1 (Compounds of Formula Ia);
b. $R_1$ is methyl or ethyl, especially those of (a);
c. At least one of $R_2$, $R_3$ and $R_4$, preferably $R_4$, is an esterified or etherified hydroxy, e.g., alkanoyloxy of 2-8 carbon atoms or alkoxy of 1-8 carbon atoms, and at least one and preferably both of the remainder are hydrogen atoms, especially those of (a) and (b);
d. X is hydroxymethylene or alkoxymethylene of 1-8 carbon atoms, preferably tert.-butoxymethylene, especially those of (a), (b), and (c); and
(e) y is carbonyl or dimethoxymethylene, especially those of (a), (b), (c) and (d).

Lower alkyl means alkyl of 1 to 6 carbon atoms. Preferred $R_1$ groups are those of 1-4 carbon atoms, e.g., methyl, ethyl, propyl, isopropyl and the butyl groups, especially methyl or ethyl.

$R_2$, $R_3$ and $R_4$ can be a hydrogen atom, an alkoxy group or an acyloxy group. Preferred such alkoxy groups are those of 1-4 carbon atoms, e.g., methoxy, ethoxy, propoxy, isopropoxy, butoxy and tert.-butoxy. Preferred such acyloxy groups are those of 1-12 carbon atoms wherein the acyl group is that of an aliphatic, cycloaliphatic or aromatic, preferably hydrocarbon, e.g., carboxylic acid, of 2-8 carbon atoms. Examples of such acyloxy groups are the acetoxy, propionyloxy, butyryloxy, trimethylacetoxy, hexanoyloxy or other alkanoyloxy, cyclopentylcarboxy or benzoyloxy group.

X can be a free or ketalized carbonyl or hydroxymethylene, which can be free, esterified or etherified, e.g., hydroxymethylene, hydrocarbonoxymethylene or hydrocarboncarbonyloxymethylene. Such ketalized carbonyl groups are dialkoxymethylene as defined for Y or preferably alkylenedioxymethylene groups of 2-6 carbon atoms and with 2-3 carbon atoms in the alkylene chain or a o-phenylenedioxymethylene group, e.g. 1,2-ethylenedioxymethylene, 1,3-propylenedioxymethylene, 2,3-butylenedioxymethylene, 2',2'-dimethyl-1',3'-propylenedioxymethylene, 2,4-pentylenedioxymethylene and 1,2-phenylenedioxymethylene. Examples of esterified hydroxymethylene groups are those wherein the ester groups have 1-10 carbon atoms, e.g., carboxylic acid groups, preferably hydrocarbon carboxylic acid ester groups, for example, acetoxy, propionyloxy, butyryloxy, trimethylacetoxy, pentanoyloxy, hexanoyloxy, heptanoyloxy, octanoyloxy and benzoyloxy. Examples of etherified hydroxymethylene groups are alkoxymethylene groups of 1-10 carbon atoms and aralkoxymethylene groups of 7-10 carbon atoms in the alkoxy and aralkoxy group, respectively, e.g., methoxy, ethoxy, propoxy, butoxy, tert.-butoxy, isopropoxy and benzyloxy.

As will be apparent to those skilled in the art, if the compounds of Formula I are to be used as intermediates for the production of steroids, when X is a free, esterified or etherified hydroxymethylene group, the oxy group is preferably of the 17β-stereo configuration, corresponding to the 17β-hydroxy group of a naturally occurring steroid.

Y can be a free carbonyl group or, like X, a ketalized carbonyl group, preferably a dialkoxymethylene group. Examples of dialkoxymethylene groups are those wherein each alkoxy group has 1–4 carbon atoms. Exampls of dialkoxymethylene groups are dimethoxymethylene, diethoxymethylene, dipropoxymethylene and dibutoxymethylene.

It will be apparent to those skilled in the art that the ether and ester groups of X, $R_1$, $R_2$, $R_3$ and $R_4$ and the ketal groups of X and Y are preferably simple and otherwise unsubstituted groups, since more complicated groups are ordinarily of little if any benefit, particularly since most of these groups are merely blocking groups which are subsequently removed to regenerate the free hydroxy or keto group. Therefore, in addition to those $R_2$, $R_3$, $R_4$, X and Y groups more precisely defined in the claims hereinafter, equivalent are those bearing one, two, three or more substituents, e.g., halo, nitro, amido, carbamide, primary, sec. or tert.-amino, alkoxy, alkanoyloxy, mercapto, sulfato, etc.; the cyclic counterparts of alkyl groups, e.g., cyclopropyl, cyclopentyl, cyclohexyl, cycloheptyl; aryl analogs of phenyl groups, e.g., naphthyl, p-tolyl, sym.-xylyl; and sulfonic ester analogs of carboxylic ester groups, e.g., methanesulfonyloxy, ethanesulfonyloxy, p-toluenesulfonyloxy and benzenesulfonyloxy.

In addition to the species of the examples hereinafter, the following are illustrative examples of the compounds of this invention:

3,17β-diacetoxy-9,10-seco-1,3,5(10),8(14)-estratetraene-6,9-dione,
3-methoxy-17β-benzyloxy-9,10-seco-1,3,5(10),8(14)-estratetraene-6,9-dione,
3,17β-dibenzoyloxy-9,10-seco-1,3,5(10),8(14)-estratetraene-6,9-dione,
3-methoxy-17,17-(2',2'-dimethyl-propylene-dioxy)-9,10-seco-1,3,5(10),8(14)-estratetraene-6,9-dione,
3-methoxy-17,17-(o-phenylene-dioxy)-9,10-seco-1,3,5(10),8(14)-estratetraene-6,9-dione,
3-methoxy-6,6-diethoxy-17β-tert.-butyloxy-9,10-seco-1,3,5(10),8(14)-estratetraen-9-one,
1,3,17β-tribenzoyloxy-9,10-seco-1,3,5(10),8(14)-estratetraene-6,9-dione
2,3,17β-trimethoxy-9,10-seco-1,3,5(10),8(14)-estratetraene-6,9-dione
3,6,6-triethoxy-17β-benzoyloxy-9,10-seco-1,3,5(10),8(14)-estratetraen-9-one,
3,17β-dihydroxy-9,10-seco-1,3,5(10),8(14)-estratetraene-6,9-dione and
3-methoxy-9,10-seco-1,3,5(10),8(14)-estratetraene-6,9,17-trione.

In the addition step of this invention, preferred basic catalysts are alkali alcoholates of secondary or tertiary alcohols, alkali hydrides, alkali amides and quaternary ammonium bases. Examples of such basic catalysts are sodium hydride, sodium amide, sodium isopropanolate, sodium tert.-butylate, potassium tert.-butylate, lithium amide, tetramethylammonium hydroxide and trimethylbenzylammonium hydroxide, in an inert solvent. It is advantageous in this reaction to employ at least 1 mole of basic catalyst per mole of tetrahydroindan of Formula II, in order to form the carbanion, and to bind the hydrogen halide liberated by the reaction with the haloacetophenone of Formula III. A somewhat elevated temperature, e.g., 30° C. up to the boiling temperature of the solvent, is preferably employed, along with a protective gas atmosphere such as, for example, nitrogen or argon.

The chemical addition of the haloacetophenones of Formula III to the compounds of Formula II is effected in an inert solvent. Suitable solvents are, for example, polar ethers, e.g., 1,2-dimethoxyethane, 2',2'-dimethoxydiethyl ether, tetrahydrofuran and dioxane, secondary or tertiary alcohols, e.g., isopropanol, 2-butanol and tert.-butanol, and dipolar aprotic solvents, e.g., dimethylformamide, N-methylacetamide, N-methylpyrrolidone and hexamethylphosphoric triamide. It is also possible to use mixtures of the above-mentioned solvents and relatively nonpolar solvents, e.g., benzene and toluene.

When X of the starting compounds of general Formula II is a free hydroxymethylene group, it is advantageous, in order to obtain higher yields, to first react it with a vinyl ether, e.g., methyl or ethyl or other alkyl vinyl ether. In this case, compounds otherwise corresponding to those of Formula II are obtained as intermediates in which X is an (1-alkoxyethyl)-oxymethylene group, e.g., (1-ethoxyethyl)-oxymethylene. This group is then split off again after the reaction has been accomplished during the working up of the reaction mixture.

The condensation of the haloacetophenones of Formula III to the tetrahydroindan derivatives of Formula II is preferably conducted at a reaction temperature of from −50° C. to +50° C., preferably −25° C. to +25° C.

It is surprising that the condensation of the compounds of Formula II with the haloacetophenones produces the 6-oxo-9,10-secoestrane derivatives of Formula I in high yields, because it is known that the condensation of compounds of general Formula I with the corresponding phenethyl halides produces 9,10-secoestrane derivatives only to very low yields. See J. Chem. Soc., 1970, 10–18.

The thus-produced compounds of general Formula I wherein Y is a free carbonyl group can optionally then be ketalized, e.g., with a lower alcohol, thus obtaining compounds of Formula I wherein the group Y is a ketalized keto, e.g., dialkoxymethylene, group. This ketalization is conducted in a conventional manner, preferably by reacting the keto compound with the selected alcohol in the presence of an acidic catalyst. Suitable alcohols are, for example, lower alkanols of 1–4 carbon atoms, e.g., methanol, ethanol, propanol and butanol. Suitable acidic catalysts include mineral acids, e.g., hydrochloric acid, sulfuric acid and perchloric acid; sulfonic acids, e.g., methanesulfonic acid; Lewis acids, e.g., boron trifluoride; and phenols, e.g., p-nitrophenol and 2,4-dinitrophenol. The ketalization is especially successful when a water-binding agent is added to the reaction mixture, e.g., anhydrous sodium sulfate, magnesium sulfate and calcium sulfate. Other waterbinding agents include orthoformic acid esters or acetone dialkyl ketals of the alcohols employed for the ketalization. The ketalization is preferably conducted at a reaction temperature of between −20° C. and +50° C.

This ketalization takes place surprisingly selectively on the oxo group in the 6-position and the oxo group in the 9-position is substantially unaffected.

The compounds of general Formula I produced in accordance with the process of this invention are valuable intermediates for the production of polycyclic compounds. They are especially suitable for the manufacture of pharmacologically effective steroids by a total synthesis.

The following reaction scheme illustrates the use of compounds of Formula I in a total steroid synthesis:

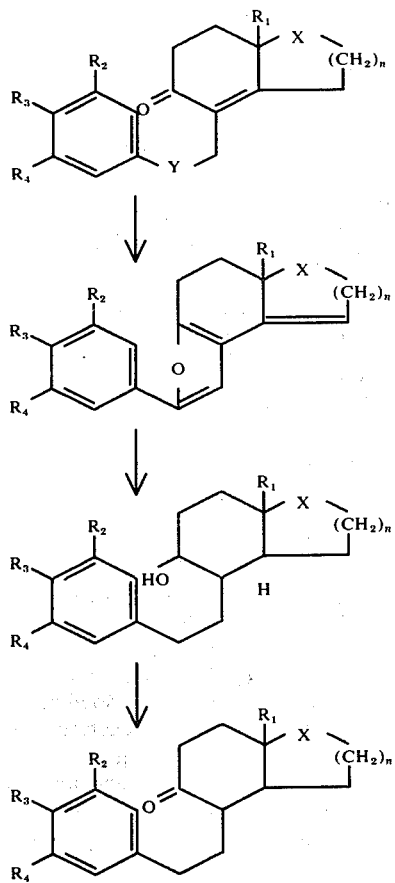

Thus, as disclosed in our copending application Ser. No. 409,235, filed Oct. 24, 1973, the disclosure of which is incorporated by reference, heating the 9,10-secoestranes of Formula I in benzene or toluene in the presence of a catalytic amount of p-toluenesulfonic acid or other acidic catalyst while simultaneously removing the thus-formed water or alcohol by distillation produces compounds of Formula IV. The latter can then be hydrogenated under pressure in an alcoholic solution with hydrogen in the presence of a palladium catalyst to produce compounds of Formula V.

The compounds of Formula V can be oxidized to the compounds of Formula VI in acetone at −10° to 0° C. with chromosulfuric acid. The conversion of compounds of Formula VI to pharmacologically active steroids can be accomplished in a conventional manner, e.g., by cyclizing the compounds of Formula VI to the corresponding estrane derivatives, optionally hydrolyzing the estrane-esters or estrane-ethers and oxidizing 17β-hydroxy-estrane-derivatives under conventional conditions (German Pat. No. 1,231,699).

The compounds of the general Formula I may be used as intermediates for the production of pharmacologically active estrane derivatives, e.g., estrone, estradiol, 2-hydroxyestrone (Steroids 4, 1964, 267), 1-hydroxy-estradiol (Arzneimittel-Forschung 16, 1966, 1518) or 3-desoxy-estrone (U.S. Pat. No. 3,081,316).

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

20 g. of 1β-tert.-butoxy-7aβ-methyl-5,6,7,7a-tetrahydroindan-5-one is dissolved in 250 ml. of absolute tetrahydrofuran. The reaction flask is then flushed with argon. After adding 2.35 g. of sodium hydride, the reaction mixture is refluxed for 10 hours, cooled to −10° C., and combined dropwise with a solution of 22.5 g. of 3'-methoxy-1-bromoacetophenone in 100 ml. of absolute tetrahydrofuran.

After a reaction time of 16 hours at −10° C. to 0° C., the solvent is distilled off under vacuum, and the reaction mixture is extracted with ether after adding 250 ml. of saturated sodium chloride solution. The ether extract is washed, dried, and concentrated under vacuum. The residue is purified by chromatography, recrystallized from diisopropyl ether, and the product is 25.1 g. of 3-methoxy-17β-tert.-butoxy-9,10-seco-1,3,5(10),8(14)-estratetraene-6,9-dione, m.p. 75° − 76.5° C.

$[\alpha]_D^{20} = -0.9°$ (chloroform; $c = 1$).

EXAMPLE 2

11.3 g. of 1β-tert.-butoxy-7aβ-ethyl-5,6,7,7a-tetrahydroindan-5-one is reacted according to Example 1 in 150 ml. of absolute dimethoxyethane with 1.3 g. of sodium hydride. Under ice cooling, a solution of 12.4 g. of 3'-methoxy-1-bromoacetophenone in 50 ml. of absolute dimethoxyethane is added dropwise within 10 minutes; subsequently, the reaction mixture is stirred for 16 hours under ice cooling.

The reaction product is worked up and purified as described in Example 1, thus obtaining 11.9 g. of 3-methoxy-17β-tert.-butoxy-18-methyl-9,10-seco-1,3,5(10),8(14)-estratetraene-6,9-dione as a colorless oil. IR bands at 5.96 μ and 6.05 μ.

$[\alpha]_D^{21} = -0.2°$ (chloroform; $c = 1$).

EXAMPLE 3

5.3 g. of 1β-tert.-butoxy-7aβ-methyl-5,6,7,7a-tetrahydroindan-5-one is reacted, as described in Example 1, first with sodium hydride in tetrahydrofuran and then with ω-bromoacetophenone. After the reaction mixture has been worked up, purified by chromatography, and recrystallized from diisopropyl ether, 5.85 g. of 17β-tert.-butoxy-9,10-seco-1,3,5(10),8(14)-estratetraene-6,9-dione is obtained, m.p. 86° − 87.5° C.

$[\alpha]_D^{21} = -0.5°$ (chloroform; $c = 1$).

EXAMPLE 4

10 g. of 1β-hydroxy-7aβ-methyl-5,6,7,7a-tetrahydroindan-5-one is dissolved in 100 ml. of absolute dimethoxyethane, and 6 g. of freshly distilled ethylvinyl ether and 10 mg. of p-toluenesulfonic acid are added thereto. The mixture is agitated for one hour at room temperature.

Thereafter, the excess ethylvinyl ether is distilled off under vacuum, and 1.7 g. of sodium hydride is added. After a reaction time of 15 hours at 70° C., the mixture is cooled to −5° C. and, within 20 minutes, a solution of 16.5 g. of 3'-methoxy-1-bromoacetophenone in 50 ml. of absolute dimethoxyethane is added dropwise thereto. After a reaction period of 16 hours under ice cooling, the mixture is gently acidified with 1N hydrochloric acid to a pH of 3, and agitated for 30 minutes at room temperature.

The light-brown product obtained after conducting the usual working-up operation is chromatographed on a silica gel column for purification purposes, thus obtaining 15.8 g. of 17β-hydroxy-3-methoxy-9,10-seco-1,3,5(10),8(14)-estratetraene-6,9-dione as a colorless oil. IR bands at 5.95 μ and 6.02 μ.

$[\alpha]_D^{21} = +13.5°$ (chloroform; $c = 1$).

EXAMPLE 5

4.6 g. of 1β-hydroxy-7aβ-ethyl-5,6,7,7a-tetrahydroindan-5-one is reacted in 60 ml. of absolute dimethoxyethane in the manner described in Example 4 first with vinylethyl ether and then with sodium hydride. Under ice cooling and agitation, 7.9 g. of 3'-methoxy-1-bromoacetophenone in 30 ml. of absolute dimethoxyethane is added dropwise to the reaction mixture within 10 minutes, and the mixture is then allowed to stand for 16 hours under ice cooling. Then, the mixture is acidified to pH 3 with 1N hydrochloric acid, worked up as disclosed in Example 4, and the product is 6.1 g. of 17β-hydroxy-3-methoxy-18-methyl-9,10-seco-1,3,5(10),8(14)-estratetraene-6,9-dione as a colorless oil. IR bands at 5.96 μ and 6.04 μ. $[\alpha]_D^{21} = +9.2°$ (chloroform; $c = 1$).

EXAMPLE 6

10 g. of 3-methoxy-17β-tert.-butoxy-9,10-seco-1,3,5(10),8(14)-estratetraene-6,9-dione is dissolved in 100 ml. of absolute methanol and 10 ml. of trimethyl orthoformate, and the solution is cooled to 0° C. Then, 50 mg. of p-toluenesulfonic acid is added and the mixture is agitated for 20 hours under ice cooling. Thereafter, the mixture is poured into 500 ml. of dilute sodium bicarbonate solution and extracted with ether. The ether phase is washed, dried and concentrated under vacuum, thus obtaining 12.3 g. of 3,6,6-trimethoxy-17β-tert.-butoxy-9,10-seco-1,3,5(10),8(14)-estratetraen-9-one as a colorless oil. IR band at 6.04 μ, no band at 5.96 μ.

EXAMPLE 7

Under the conditions of Example 1, 1β-tert.-butoxy-7aβ-methyl-5,6,7,7a-tetrahydroindan-5-one can be condensed with ω-bromo-3,5-dimethoxy-acetophenone to give 1,3-dimethoxy-17β-tert.-butoxy-9,10-seco-1,3,5(10),8(14)-estratetraene-6,9-dione which can be ketalized under the conditions of Example 6 to give 1,3,6,6-tetramethoxy-17β-tert.-butyloxy-9,10-seco-1,3,5(10),8(14)-estratetraen-9-one.

EXAMPLE 8

Under the conditions of Example 1, 1β-tert.-butoxy-7aβ-methyl-5,6,7,7a-tetrahydroindan-5-one can be condensed with ω-bromo-3,4-dimethoxy-acetophenone to give 2,3-dimethoxy-17β-tert.-butoxy-9,10-seco-1,3,5(10),8(14)-estratetraene-6,9-dione.

EXAMPLE 9

20 g. of 1β-benzoyl-7aβ-methyl-5,6,7,7a-tetrahydroindan-5-one is dissolved in 250 ml. of absolute tetrahydrofuran. The reaction flask is then flushed with argon. After adding 9.0 g. of potassium tert.-butylate, the reaction mixture is refluxed for 2 hours, cooled to −10° C., and combined dropwise with a solution of 22.5 g. of 3'-methoxy-1-bromoacetophenone in 100 ml. of absolute tetrahydrofuran.

After a reaction time of 16 hours at −10° C. to 0° C., the solvent is distilled off under vacuum, and the reaction mixture is extracted with ether after adding 250 ml. of saturated sodium chloride solution. The ether extract is washed, dried, and concentrated under vacuum. The residue is purified by chromatography, and the product is 3-methoxy-17β-benzoyloxy-9,10-seco-1,3,5(10),8(14)-estratetraene-6,9-dione, m.p. 75° − 75.5° C.

$[\alpha]_D^{20} = -0.9°$ C. (chloroform $c=1$).

EXAMPLE 10

20 g. of 1β-benzoyloxy-7aβ-methyl-5,6,7,7a-tetrahydroindan-5-one is reacted according to Example 9 in 250 ml. of absolute dimethoxyethane with 9.0 g. of potassium tert.-butylate. Under ice cooling, a solution of 22.0 g. of 3'-benzoyloxy-1-bromoacetophenone in 100 ml. of absolute dimethoxyethane is added dropwise within 10 minutes; subsequently, the reaction mixture is stirred for 16 hours under ice cooling.

The reaction product is worked up and purified as described in Example 9, thus obtaining the 3,17β-dibenzoyloxy-9,10-seco-1,3,5(10),8(14)-estratetraene-6,9-dione.

EXAMPLE 11

10 g. of 3-methoxy-17β-benzoyloxy-9,10-seco-1,3,5(10),8(14)-estratetraene-6,9-dione is dissolved in 100 ml. of absolute methanol and 10 ml. of trimethyl orthoformate, and the solution is cooled to 0° C. Then, 50 mg. of p-toluenesulfonic acid is added and the mixture is agitated for 20 hours under ice cooling. Thereafter, the mixture is poured into 500 ml. of dilute sodium bicarbonate solution and extracted with ether. The ether phase is washed, dried and concentrated under vacuum, thus obtaining the 3,6,6-trimethoxy-17β-benzoyloxy-9,10-seco-1,3,5(10),8(14)-estratetraen-9-one.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A 9,10-secoestrane of the formula

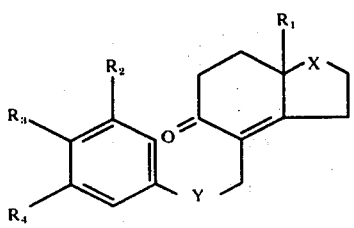

wherein $R_1$ is methyl or ethyl; $R_2$ and $R_3$ each is a hydrogen atom or alkoxy of 1–4 carbon atoms; $R_4$ is a hydrogen atom, alkoxy of 1–4 carbon atoms, or hydrocarboncarbonyloxy of 1–12 carbon atoms; X is carbonyl, dialkoxymethylene wherein the alkoxy groups each contain 1–4 carbon atoms, hydroxymethylene, alkoxymethylene wherein the alkoxy group contains 1–10 carbon atoms, or aralkoxymethylene wherein the aralkoxy group contains 7–10 carbon atoms, or hydrocarboncarbonyloxymethylene wherein the hydrocarboncarbonyloxy group contains 1–10 carbon atoms, and Y is carbonyl or dialkoxy methylene, provided that $R_4$ is hydrocarboncarbonyloxy when X is other than hydrocarbon-carbonyloxymethylene.

2. A compound of claim 1, wherein $R_1$ is methyl.
3. A compound of claim 1, wherein $R_4$ is alkanoyloxy of 2–8 carbon atoms, and $R_2$ and $R_3$ are hydrogen atoms.
4. A compound of claim 1, wherein Y is carbonyl or dimethoxymethylene.

* * * * *